United States Patent [19]

Schwartz

[11] 4,202,882
[45] May 13, 1980

[54] NOVEL DEODORIZING METHOD

[76] Inventor: Herbert Schwartz, 1963 N. Maurice River Pkwy., Vineland, N.J. 08360

[21] Appl. No.: 624,319

[22] Filed: Oct. 21, 1975

Related U.S. Application Data

[63] Continuation-in-part of Ser. No. 420,970, Dec. 3, 1973, abandoned.

[51] Int. Cl.$^2$ .............................................. A61L 13/00
[52] U.S. Cl. ...................................... 424/76; 424/244; 424/249; 424/329
[58] Field of Search .................. 424/76, 324, 244, 249

[56] References Cited

U.S. PATENT DOCUMENTS

| | | | |
|---|---|---|---|
| 2,541,248 | 2/1951 | Hibbs | 424/76 X |
| 3,198,251 | 8/1965 | Shore | 424/76 |
| 3,282,776 | 11/1966 | Kitzke et al. | 424/76 X |
| 3,419,562 | 12/1968 | Wakeman | 424/76 X |

OTHER PUBLICATIONS

Berichte vol. 25, pp. 2711-2713; & vol. 32, p. 245-247.
Chemical Abstracts 52:17632d (1958)
Chemical Abstracts 53:4777i (1959)
Chemical Abstracts 7th Call Index, 22387s 1962-1966.

*Primary Examiner*—Leonard Schenkman
*Attorney, Agent, or Firm*—Hammond & Littell, Weissenberger and Muserlian

[57] ABSTRACT

A method of combatting offensive odors comprising contacting the odorant with a solution containing a quaternary ammonium salt catalyst with a tetracyclic heterocycle containing four nitrogen atoms which is capable of removing malodors by reaction therewith.

6 Claims, No Drawings

NOVEL DEODORIZING METHOD

PRIOR APPLICATION

This application is a continuation-in-part of my copending application Ser. No. 420,970 filed Dec. 3, 1973 now abandoned.

STATE OF THE ART

As population increases, there is a concurrent increase in air pollution. The term "air pollution" includes toxic substances in the air and malodors. Of course, the toxic substances could be odorless but may not be, and the malodors could be either toxic or safe at the concentrations present.

How to overcome the unpleasant, annoying, and, at times to many, nauseating odors such as occur about urinals, toilet bowls, lavatories, and in public and even private rest-rooms generally, in garbage containers and collecting areas, in conveyances for transportation of various high water content and readily decomposable foodstuffs such as raw seafood and meats, of livestock, and the like, of hides and other materials that leave uncomfortable and unbearable odors, has been a constantly disturbing and troublesome problem, for such as the fetid odors of garbage and sewage could present a health problem to the community by attracting disease-carrying insects and other vermin.

Various attempts have been made to overcome that problem such as by washing and scrubbing with various cleansing agents, applying oxidizing agents and/or mere pleasant smelling preparations. However, all of these have been unsatisfactory for various reasons. Among them are cost such as for materials, labor, and time required, need to repeat and repeat the treatment because of its extremely short relief period or because the underside odor only is masked. In the latter case then, the masking agent must be constantly present by regular and all too frequent replenishment. Moreover, such odor-masking agents cannot be used where they might be contacted, or their vapors absorbed, by foodstuffs. Recently, however, attempts are being made to alter the chemistry of odorants so that they are no longer annoying to the human nose. These methods consist of thermal oxidation and chemical oxidation with ozone, chlorine, potassium permanganate, etc. The value of such procedures is questionable since the odorless products could be more injurious to health than the original malodors. The use of quaternary ammonium salts for the control of odors by direct reaction with certain odorants has been known for some time, but U.S. Pat. No. 3,198,251 of Aug. 3, 1965, teaches that in the case of the usual quaternary ammonium salts they did give some odor control, but while giving some relief from odors, such relief was inadequate and unsatisfactory.

Although the oxidation of odorants is an attempt at odor control rather than masking, it has serious defects causing adverse effects on the environment. Odorants as a group contain many compounds, some of which contain either nitrogen or sulfur or both, usually in the reduced state, e.g. sulfides, mercaptans, skatoles, amines, etc. The thermal and cold oxidation of these odoriferous compounds could yield the toxic oxides of sulfur and nitrogen while with the thermal oxidation process the yield of nitrogen oxides would be somewhat higher since the high temperatures cause oxidation of atmospheric nitrogen as well. Lower temperatures have been found to give incomplete oxidation of the organic compounds to yield such toxic products as carbon monoxide, aldehydes, acids, ketones, and water.

Chemical oxidation is usually carried out in an aqueous system, primarily in wet scrubbers. The volatile oxidation products would then be carried through the system and out the exhaust system into the environment. The U.S. Environmental Protection Agency on Apr. 18, 1975, issued a report showing that when organic compounds come into contact with aqueous chlorine, volatile organochlorine compounds are produced that are suspected carcinogens, and so the use of chlorine or hypochlorite in wet scrubbers could be considered a dangerous practice. Another oxidizing agent used in wet scrubbers is potassium permanganate, which is thereby reduced to manganese dioxide. The insoluble managanese dioxide precipitates out of solution and can eventually plug or coat the packing and severely restrict the air flow through the unit. (Industrial Odor Technology Assessment by Cheremisinoff & Young, Page 416). Since other methods have similar drawbacks, chemical oxidation may be some improvement over thermal oxidation but not a full and safe solution to the problem.

OBJECTS OF THE INVENTION

It is an object of this invention to provide novel deodorizing compositions.

It is another object of the invention to provide a novel method of combatting odors by reaction of the odor causing component with a heterocycle.

THE INVENTION

The novel method of the invention of combatting offensive odors comprises contacting the odor causing component with a composition comprising a quaternary ammonium salt and a tetracyclic heterocycle having 4 nitrogen atoms. The mode of action is believed to be the reaction of the heterocycle with the quaternary ammonium salt to obtain a complex which then reacts with the odor causing component to form a nonoffensive odor component. Without the presence of the quaternary ammonium salt, the reaction will not proceed at a sufficient rate of speed to prevent the offensive odors.

The novel deodorizing compositions are comprised of a mixture of a tetracyclic heterocycle containing four nitrogen atoms and a quaternary ammonium salt. The compositions may be in any suitable form such as solutions, suspensions, sprays, concentrates, emulsions, powders, etc.

Various quaternary ammonium salts are known to have a slight deodorizing ability and are even used commercially for this purpose since there is no satisfactory product available for this application. The primary function of these salts is that of a germicide killing the bacteria responsible for the decomposition of organic matter thereby generating odors. These salts are generally prepared by causing the reaction of a benzyl or alkyl halide, sulfonate, or sulfate with a ternary base (e.g. a tertiary amine). The usual salts are the halides, such as chloride and bromide, sulfates, methosulfates, ethosulfates, and benzenesulfonates.

Among the preferred quaternary ammonium salts for the compositions of the invention are those having the formula

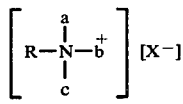

wherein R is an aliphatic radical of 8 to 20 carbon atoms, X is any anion such as halide, sulfate, nitrate, carbonate, phosphate, lower alkyl sulfate, lower alkanesulfonate, saccharinate, sulfamate, benzenesulfonate, lower alkylbenzenesulfonates with 1 to 10 alkyl carbon atoms, etc., and a, b and c may different and are selected from the group consisting of lower alkyl, phenyl lower alkyl, phenoxy lower alkyl, thenyl, lower alkenyl, lower alkynyl, substituted phenyl lower alkyl, and a and b could form a heterocyclic ring with c being an aliphatic radical of 1 to 20 carbon atoms. These and other suitable quaternary ammonium salts are described in Schwartz et al, Surface Active Agents and Detergents, Vol. II, (1958), pp. 112–118. The term "lower" is intended to mean 1 to 7 carbon atoms.

Examples of specific quaternary ammonium salts are BTC 2125 M (equal parts of n-alkyl dimethyl benzyl ammonium chlorides where the n-alkyl is 14 to 18 carbon atoms and n-alkyl dimethyl ethyl benzyl ammonium chlorides where n-alkyl is 12 to 14 carbon atoms), BTC 1100 (n-dodecyl dimethyl l-naphthylmethyl ammonium chloride monohydrate), BTC 471 (alkyl dimethyl benzyl ammonium chloride), Hyamine 1622 (diisobutyl phenoxy ethoxyethyl dimethyl benzyl ammonium chloride), Hyamine 2389 (80% of methyl dodecyl benzyl trimethyl ammonium chloride and 20% of methyl dodecyl xylene bis-trimethyl ammonium chloride), Barquat MS100 [alkyl dimethyl benzyl ammonium chloride dihydrate] etc. Although most commercial quaternary ammonium salts are the chlorides, other salts are just as suitable for the present invention.

The tetracyclic, cage-type heterocycles, i.e. heterocycles with four rings and each ring sharing its sides with the other three three rings forming an enclosed hollow center similar to adamantane, are prepared by the condensation of formaldehyde with ammonia or a primary diamine in which the two amino groups are separated by an alkylene chain of one to four carbon atoms yielding heterocycles containing four nitrogen atoms. Examples of suitable diamines are ethylenediamine, propylenediamine, o-phenylenediamine, methylenediamine (formed in situ by the action of ammonia on formaldehyde), etc. Specific heterocycles prepared and tested to represent the derivatives of both aromatic and aliphatic diamines were hexamethylenetetramine, 4(5),9(10)-dimethyl-1,3,6,8-tetraazatricyclo [4,4,1,1$^{3.8}$] decane, 1,3,6,8-tetraazatricyclo-[4,4,1,1$^{3.8}$] dodecane [Beilstein IV, p. 250 and Berichte, Vol. 31, p. 3254], and 4,5,9,10-dibenzo-1,3,6,8-tetraazatricyclo-[4,4,1,1$^{3.8}$] dodecane [Berichte, Vol. 25, p. 2711 and Vol. 32, p. 245].

There is no commercial application of any of these heterocycles for the control of malodors of any type or from any source. In fact, experimental evidence indicates that they do not control, absorb, or affect malodors in any way. Thus, it was most surprising to find that these heterocycles could indeed absorb or react with malodors if a catalytic amount of a quaternary ammonium salt were present. Practical application of this invention requires a greater amount of the quaternary ammonium salt since the products of the invention can be used at great dilutions. Sufficient quaternary ammonium salt must be available so that a molecule of the quaternary ammonium salt is available to catalyze each contact of a molecule of malodor causing component with an heterocyclic molecule. Accordingly, the ratios of heterocycle to quaternary ammonium salt can vary as much as 10:1 to 1:10 depending upon the application although it was found that for reasons of solubility and physical characteristics the usual ratios will be 5:1 to 1:5. However, this is not to be interpreted as indicating that the higher ratios are not operative but that they are reserve for special applications.

The compositions of the invention may contain any conventional carrier such as water, aqueous alkanols, alkanols, organic solvents, wetting agents, emulsifiers, perfumes, and other standard ingredients for commercial products and formulations.

The preferred novel method for controlling malodors comprises contacting the malodor causing component with a stoichiometric amount of a cage-type, nitrogen-containing heterocycle and quaternary ammonium salt. Such mixtures can economically be used in wet scrubbers to remove the malodors from exhausted air.

The novel method of the invention for removing odors from the air may also be effected by the dilution or solution of the mixture of the cage-type tetracyclic heterocycle containing four nitrogen atoms plus a quaternary ammonium salt and the dispersion of this solution through the air by fogging and/or spraying or by directly spraying the source of the odor. Examples are rendering plants, kennels, manure or sewage lagoons, field toilets, etc. Other methods may include washing and immersion of the odor source.

In the following examples there are described several preferred embodiments to illustrate the invention. However, it should be understood that the invention is not intended to be limited to the specific embodiments.

EXAMPLE 1

A solution of 25 parts by weight of hexamethylenetetramine in 52 parts by weight of water was added to a solution of 0.5 parts by weight of perfume, 10.0 parts by weight of a polyethylene oxide-alkylphenol adduct as an emulsifier, and 12.5 parts by weight of technical (80%) alkyldimethylbenzylammonium chloride (alkyl of 12 to 16 carbon atoms) to form a clear solution. This solution was dripped into a lagoon of wash water from a plant that processes chickens from the live fowl to dressed poultry and chicken parts. The plant would collect the wash water from the cleaning of the chickens and the daily wash-up, thus containing blood, fats, dirt, etc., in a large lagoon of about 190,000 liters with sufficient drainage to keep its contents constant. The full quantity of water flushed through is approximately 760,000 liters daily. The product of this invention was dripped into this lagoon at the rate of 220 kilograms every 3 months to control completely the foul odor that usually spreads throughout the neighborhood of this lagoon.

EXAMPLE 2

The solution of Example 1 was prepared with the exception of the heterocycle so that the 1,3,6,8-tetraazatricyclo [4,4,1,1$^{3.8}$] dodecane was substituted. After dilution of this product 440 times with water, the resulting solution was sprayed about the interior of chicken coops and particularly on the manure covered floors. This treatment deodorized the coops to the point that it was difficult to believe that chicken had ever been in the coops.

EXAMPLE 3

The solution of Example 1 was prepared with 4,5,9,10-dibenzo-1,3,6,8-tetraazatricyclo [4,4,1,1,$^{3.8}$] dodecane as the heterocycle. After dilution of this solution 400 times with water, the resulting solution was sprayed over piled chicken manure intended for use as fertilizer. Within 15 minutes strong odor control was detected, and just a few minutes later the entire pile had been deodorized.

EXAMPLE 4

A solution of 25 parts by weight of hexamethylenetetraamine in 75 parts by weight of water was added to a solution of 125 parts by weight of technical (80%) alkyldimethylbenzylammonium chloride (alkyl 8 to 18 carbon atoms), 100 parts by weight of polyethylene oxide-alkylphenol adduct, 25 parts by weight of perfume, 30 parts by weight of p-dichlorobenzene, and 120 parts by weight of o-dichlorobenzene to form a clear solution. This solution was then diluted 10 times with alcohol and placed in aerosol cans with the correct amount of propellant of the Freon type (halocarbon). A wine cellar was sprayed thoroughly with this aerosol, and the typical musty odor was eliminated for over 6 months.

EXAMPLE 5

A solution of 5 parts by weight of p-dichlorobenzene in 10 parts by weight of o-dichlorobenzene was added to a solution of 72 parts by weight of a 35% solution (in anhydrous alcohol) of N,N-cetylethylmorpholinium ethosulfate, 10 parts by weight of N,N-diethyl-m-toluamide, 23 parts by weight of polyethylene oxide-alkylphenol adduct, 255 parts by weight of alcohol, 50 parts by weight of hexamethylenetetramine, 75 parts by weight of water, and 25 parts by weight of perfume to make a clear solution. This solution was then diluted 10 times with alcohol and placed in aerosol cans along with Freon type propellant. This aerosol was applied to a dog that had had an unfortunate encounter with a skunk. One application neutralized about 80% of the odor, and a second application eliminated the odor completely.

EXAMPLE 6

A solution of 5 parts by weight of hexamethylenetetramine, 20 parts by weight of alkyldimethylbenzylammonium chloride, 43 parts by weight of water, 2 parts by weight of sodium carbonate, 15 parts by weight of polyethylene oxide-alkylphenol adduct, 14 parts by weight of technical N,N-diethanolamides of long-chain fatty acids, and 1 part by weight of perfume was prepared and then diluted with water 400 times. This dilute solution was then applied to the floor and walls of animal cages. This single application removed the clinging odors of animal wastes (both liquid and solid) from both dogs and cats.

EXAMPLE 7

The product of Example 6—after proper dilution—was used to deodorize trucks that had transported live poultry and dead animals or animal parts to rendering plants.

EXAMPLE 8

A solution containing 6 parts by weight of hexamethylenetetramine, 2.5 parts by weight of 80% alkylidimethylbenzylammonium chloride, 0.5 parts by weight of sodium acetate, 2 parts by weight of sodium carbonate, 0.5 parts by weight of perfume, 2.5 parts by weight of N,N-diethanolamide of long chain fatty acids (up to 18 carbon atoms), 5 parts by weight polyethylene oxide-alkylphenol adduct, 20 parts by weight of sodium lauryl sulfate concentrate (35% active), and 61 parts by weight of water was prepared. This product was diluted 1 part by weight of product to 30 parts by weight of water to make a deodorizing detergent solution for both cleaning and elimination of odors. This cleaning solution was used in kitchens, butcher shops, kennels, and the concentrate in special dispensing bottles in toilets for deodorizing and cleaning as used.

EXAMPLE 9

A solution containing 25 parts by weight of hexamethylenetetramine, 25 parts by weight of 80% alkyldimethylbenzylammonium chloride (alkyl 8 to 18 carbon atoms), 5 parts by weight of polyethylene oxide-alkylphenol adduct, 8 parts by weight of perfume, 0.2 parts by weight of a water-soluble blue dye, and 36.8 parts by weight of water was added to a recirculating toilet of the type used on boats, trailers, and campers. For toilets with a capacity of 37.8 liters, 680 grams of this product was added along with 11.34 liters of clean water, after which the toilet was used for 2 weeks with complete odor control. Similar odor control was obtained with 115 grams of this product in a recirculating toilet with a capacity of 15 liters.

EXAMPLE 10

A mixture containing 25 parts by weight of hexamethylenetetramine, 15 parts by weight of alkyldimethyl (1-naphthylmethyl)-ammonium chloride (alkyl has 12 to 14 carbon atoms) monohydrate, 10 parts by weight of sodium lauryl sulfate was prepared as a dry formulation. This powder was then blended into kitty litter at an approximate dilution of 1 part to 1100 parts by weight of the kitty litter, after which the treated kitty litter was used in the normal manner by an adult cat. After 1 week's use, there was no odor emanating from the litter.

EXAMPLE 11

A solution containing 96.8 parts by weight of hexamethylenetetramine, 60.5 parts by weight of 80% alkyldimethylbenzylammonium chloride (alkyl has 8 to 18 carbon atoms), 36.3 parts by weight of technical 2-alkyloxazoline (alkyl has 8 to 18 carbon atoms), 24.2 parts by weight of perfume, 24.2 parts by weight of 30% silicone defoamer, and 242.1 parts by weight of water was prepared as a non-foaming product. This product was added at a rate of 7.5 to 9.5 liters to 9450 liters of water in a wet scrubber through which the exhausted air from a rendering plant must pass. With the use of this product in this manner, the air was rendered odorless for 2 days. The non-foaming property was necessary in view of the strong agitation of the solution in the scrubber; the other products would fill the scrubbing system with foam.

EXAMPLE 12

The product of Example 11 was diluted at the rate described therein, i.e. 4.5 to 6 liters in 5900 liters of water, for use in street cleaning equipment to deodorize 1 kilometer of city streets. The concentration was doubled to deodorize the streets around an old fish market.

EXAMPLE 13

A solution of 96.8 parts by weight of hexamethylenetetramine, 58.08 parts by weight of 80% alkyltrimethylbenzylammonium chloride (alkyl has 8 to 18 carbon atoms), 96.8 parts by weight of polyethylene-oxide-alkylphenol adduct, 24.2 parts by weight of perfume, 19.36 parts by weight of 2-ethyl-1,3-hexanediol, 16.2 parts by weight of o-dichlorobenzene, 8 parts by weight of p-dichlorobenzene, and 164.56 parts by weight of water was prepared. The daily addition of 7.5 liters of this product to 5670 liters of water in the wet scrubber of a rendering plant prevented the passage of malodors through the scrubber and out of the plant. The daily addition of the product was necessary since the system replaced the solution with 11.3 to 18.9 liters of fresh water every minute.

EXAMPLE 14

The product of Example 13, when diluted 1 part to 440 parts by weight of water, can be sprayed into a truck, trailer, or other cargo container in which spoiled food or seafood had left a lingering odor that cannot be washed out. A truck had stood in the hot sun for 2 weeks after the refrigeration unit had broken down. Although the truck was unloaded and washed out, a repulsive odor prevented further use of the truck, but the interior was then sprayed with this solution and closed for 30 to 40 minutes. When opened, the container had no trace of odor and could be used almost immediately for the transportation of more food.

EXAMPLE 15

Using the dilution of Example 14, the product was found to remove the odor of smoke from clothes and building after a fire. Likewise the solution was fogged into the stacks of a municipal incinerator to deodorize the exhausted air.

EXAMPLE 16

Using the dilution of Example 14, sufficient product was placed in the vaults of park latrines to cover the bottom to a depth of several centimeters. The latrine remained odor free between clean-ups.

EXAMPLE 17

An odor panel was convened for the purpose of comparing the deodorizing properties of hexamethylenetetramine solution with those of the same solution containing benzalkonium chloride. The panel consisted of four persons.

The odors to be controlled were derived from rancid cottage cheese (a) and decayed mushrooms (b). The odor-producers were placed in contact with pieces of waxed cardboard which absorbed the odors but not the substances of nonvolatile nature. Contact time was over 24 hours and then two solutions were prepared. Solution #1 consisted of 20% of hexamethylenetetramine in water while Solution #2 was a solution of 20% of hexamethylenetetramine and 10% of alkyldimethylbenzylammonium chloride (alkyl of 12 to 16 carbon atoms).

Each solution was diluted four times and then was sprayed over the pieces of cardboard with a vaporizer. The odor panel was not present at this time. Five minutes later the odor panel was allowed into the room one at a time and the verdict was recorded privately. Each panel member sniffed each piece of paper separately with a separate verdict for each. The results were recorded in Table I.

TABLE I

| Panel member | Solution #1 | | Solution #2 | |
| --- | --- | --- | --- | --- |
| | a | b | a | b |
| A | + | + | − | − |
| B | + | + | − | − |
| C | + | + | − | − |
| D | + | + | − | − | where + = strong odor
− = no odor

This experiment showed that hexamethylenetetramine alone had no deodorizing properties although the combination of this substance with a quaternary ammonium salt did. Although quaternary ammonium salts do have some deodorizing properties, U.S. Pat. No. 3,198,251 proves that these are inadequate. Although the odors involved in this test were derived from the degradation of foods through the actions of atmospheric oxygen and bacteria, no attempt was made to prevent the formation of future odors by killing the bacteria but merely to counteract the odor already formed.

EXAMPLE 18

An odor panel was convened for the purpose of comparing the deodorizing properties of the combination of hexamethylenetetramine and a benzalkonium chloride in solution with solutions containing only one of the components. The panel consisted of four persons.

The odor to be controlled was a sample of rendering plant distillate which is the result of the condensation of the vapors coming from the cookers in a rendering plant. This condensate is a clear liquid which is fairly sterile in view of the high temperatures of the cookers.

Three solutions were prepared: (1) 20% of hexamethylenetetramine in water, (2) 20% of hexamethylenetetramine and 10% of the benzalkonium chloride of the first test in water, and (3) 10% of the benzalkonium chloride itself in water. Four beakers were filled with 50 ml of distillate and 50 ml of water. The first was the control while the 3 others received 10 ml each of the above test solutions according to the number, i.e. the first test beaker received Solution #1 etc. The odor panel saw only the number with no knowledge of the contents.

ODOR RATINGS:
0 = no odor
1 = slight odor (not unpleasant)
2 = unpleasant odor
3 = strong, unpleasant odor
4 = unbearable, objectional odor The results of the test were unanimous according to the panel. The ratings by number are the following:

| | Rating |
| --- | --- |
| Control | 4 |
| Solution #1 | 3 |
| Solution #2 | 1 |

| | Rating |
|---|---|
| Solution #3 | 2 |

This experiment found that the quaternary ammonium salt did have some deodorizing property but insufficient for the control of strong odors as stated in the U.S. Pat. No. 3,198,251. Hexamethylenetetramine is even less effective than the quaternary ammonium salt although it does show some slight effect. The differences between the odor ratings could be described as logarithmic since the jump from 2 to 1 is very large, much larger than from 3 to 2, and the difference between 3 and 4 is rather small; thus the result of the combination is not additive. According to the consulting engineers FISKE-GAY ASSOCIATES, a rating of "1" would be satisfactory since nothing else tested even approached this rating.

EXAMPLE 19

The product of Example 1 was used in a wet scrubber for exhaust gases for a spent grain dryer in a brewery. The composition was used at the ratio of one-half pint, one pint and one and one-half pints per 150 gallons of scrubber water. The results were 97.9%, 98.8%, and 99% reduction respectively of the odors.

Various modifications of the products and compositions of this invention may be made without departing from the spirit or scope thereof, and it is to be understood that the invention is to be limited only as defined in the appended claims.

I claim:

1. A method of combatting odors comprising contacting the odor causing compounds with an amount sufficient to combat odors of a composition consisting essentially of a tetraazaheterocycle selected from the group consisting of hexamethylenetetramine, 1,3,6,8-tetraazatricyclo [4,4,1,1$^{3.8}$]dodecane and 4,5,9,10-dibenzo-1,3,6,8-tetraazatricyclo[4,4,1,1$^{3.8}$]dodecane and a quaternary ammonium salt, the ratio of heterocycle to quaternary ammonium salt being 10:1 to 1:10.

2. The method of claim 1 wherein the said ammonium salt has the formula

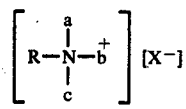

wherein R is aliphatic of 8 to 20 carbon atoms, X is an anion selected from the group consisting of halide, sulfate, nitrate, carbonate, phosphate, lower alkyl sulfate, lower alkane sulfonate, saccharinate, sulfamate, benzene sulfonate and alkylbenzene sulfonate with 1 to 10 alkyl carbon atoms and a,b and c and individually selected from the group consisting of lower alkyl, phenoxyl lower alkyl, thenyl, lower alkenyl, lower alkynyl and phenyl lower alkyl.

3. The method of claim 2 wherein the ratio is 5:1 to 1:5.

4. The method of claim 1 wherein the heterocycle is hexamethylenetetraamine.

5. The method of claim 1 wherein the heterocycle is 1,3,6,8-tetraazatricyclo[4,4,1,1$^{3.8}$[dodecane.

6. The method of claim 1 wherein the heterocycle is 4,5,9,10-dibenzo-1,3,6,8-tetraazatricyclo[4,4,1,1$^{3.8}$]dodecane.

* * * * *